US008262765B2

(12) United States Patent
Summer et al.

(10) Patent No.: US 8,262,765 B2
(45) Date of Patent: Sep. 11, 2012

(54) METHOD OF PREPARING A CONTROLLED RELEASE FERTILIZER

(75) Inventors: Paul Summer, Oskaloosa, IA (US); Randall Vos, New Sharon, IA (US)

(73) Assignee: Ajinomoto North America, Inc., Fort Lee, NJ (US)

( * ) Notice: Subject to any disclaimer, the term of this patent is extended or adjusted under 35 U.S.C. 154(b) by 180 days.

(21) Appl. No.: 12/538,358

(22) Filed: Aug. 10, 2009

(65) Prior Publication Data

US 2010/0035308 A1    Feb. 11, 2010

Related U.S. Application Data

(60) Provisional application No. 61/087,370, filed on Aug. 8, 2008.

(51) Int. Cl.
| *C05D 9/02* | (2006.01) |
| *C05D 9/00* | (2006.01) |
| *C05F 11/00* | (2006.01) |
| *C05F 7/00* | (2006.01) |
| *C05B 7/00* | (2006.01) |
| *C05B 17/00* | (2006.01) |

(52) U.S. Cl. ............. 71/23; 71/11; 71/25; 71/31; 71/32; 71/33

(58) Field of Classification Search ................ 71/11, 23, 71/25, 31–60
See application file for complete search history.

(56) References Cited

U.S. PATENT DOCUMENTS

| 3,320,048 | A | | 5/1967 | Legal et al. |
| 5,294,348 | A | * | 3/1994 | Horny et al. ................. 210/724 |
| 6,506,805 | B2 | * | 1/2003 | Green et al. ................. 516/88 |
| 6,776,816 | B1 | | 8/2004 | Ringelberg et al. |
| 8,017,365 | B1 | * | 9/2011 | Rein et al. ................. 435/161 |
| 2010/0035308 | A1 | * | 2/2010 | Summer et al. ............. 435/115 |

FOREIGN PATENT DOCUMENTS

| DE | 3732896 A1 | * | 8/1988 |
| EP | 287152 A1 | * | 10/1988 |
| EP | 335280 A1 | * | 10/1989 |

OTHER PUBLICATIONS

Lumpkins, "Nutritional value and use of distiller's dried grains with solubles in the feeding of poultry". The University of Florids, 2002.*
"Ethanol plants could use anaerobic digestion to make methane and fertilizer from corn stillage," AURI, AgInnovation Update, AURI on the Web, www.auri.org, Mar. 2008, two (2) pages.
"Home Products & Markets Wastewater Treatment Crystal Green", OSTARA, http//www.ostara.com/?g=node/11, 2009, two (2) pages.
I. Stratful et al, "Conditions Influencing the Precipitation of Magnesium Ammonium Phosphate", Wat. Res. vol. 35, No. 17, 2001, pp. 4191-4199.
A. E. Johnston et al, "Effectiveness of Different Precipitated Phosphates as Phosphorus Sources for Plants" Phosphorus Research Bulletin, vol. 15, 2004, pp. 52-59.
Sanussi Y. Ahmed et al,"Use of Struvite, a Novel P Source Derived from Wastewater Treatment, in Wheat Cultivation." 18$^{th}$ World Congress of Soil Science, Jul. 9-15, 2006, 154-33, one (1) page.

* cited by examiner

*Primary Examiner* — Stanley Silverman
*Assistant Examiner* — Jennifer Smith
(74) *Attorney, Agent, or Firm* — Oblon, Spivak, McClelland, Maier & Neustadt, L.L.P.

(57) ABSTRACT

Methods of preparing a controlled release fertilizer include obtaining an amino acid fermentation byproduct liquor, and converting ammonium in the amino acid fermentation byproduct liquor to magnesium ammonium phosphate to obtain the controlled release fertilizer.

17 Claims, No Drawings

METHOD OF PREPARING A CONTROLLED RELEASE FERTILIZER

CROSS REFERENCE TO RELATED APPLICATIONS

This application claims priority to U.S. Provisional Patent Application No. 61/087,370, filed Aug. 8, 2008, the disclosure of which is incorporated herein by reference in its entirety.

BACKGROUND

Controlled or slow release fertilizers are fertilizers that include a plant nutrient in a form that delays availability of that nutrient for plant uptake and use after application. That is, a controlled or slow release fertilizer extends availability of a constituent plant nutrient beyond that of a rapidly available nutrient fertilizer. Rapidly available nutrient fertilizers that are sources of nitrogen include ammonium nitrate, urea, ammonium phosphate, and/or potassium chloride (The Association of American Plant Food Control Officials' Publication 1985).

The delay of initial availability or extended time of continued availability that are possible with controlled or slow release fertilizers occur by a variety of mechanisms. One such mechanism relates to controlled water solubility of the pertinent plant nutrient. Control of water solubility can be effected by employing, for example, semipermeable coatings or occlusion. Control of water solubility may also be effected by relying on the inherent water insolubility of certain polymers, natural nitrogenous organics, protein materials, or other chemical forms. Further means for controlling water solubility include relying on the slow hydrolysis of water soluble low molecular weight compounds (The Association of American Plant Food Control Officials' Publication 1985).

Rapidly available nutrient fertilizers provide a large amount of a plant nutrient at one time. This large dose of plant nutrient can lead to large flushes of growth immediately following application, which can be undesirable. This effect can be mitigated by applying small doses of the fertilizer sequentially over time. However, adopting such a strategy involves multiple applications, increasing the time and cost associated with growing. To address this difficulty, controlled or slow release fertilizers are used in conjunction with rapidly available nutrient fertilizers to allow for fewer applications, while achieving an even plant nutrient release rate. This strategy decreases the occurrence of flushes of growth, as mentioned above, and reduces the environmental effects associated with leaching that can occur when a single, large application of rapidly available nutrient fertilizer is employed. Controlled or slow release fertilizers, when used correctly, allow for the single application of fertilizer with the effect of multiple small applications of a rapidly available nutrient fertilizer.

Struvite, also known as magnesium ammonium phosphate hexahydrate, is a compound that is commonly found as a precipitate on pipes. Much investigation has been done on struvite to avoid its accumulation in pipes, but there has also been work relating to enhancing struvite precipitation in waste water to decrease phosphorus load. The struvite precipitate can then be dried and used as a phosphorus rich fertilizer source. Struvite is a desirable fertilizer because of its low solubility in water, which confers a controlled or slow release nature to the fertilizer.

Various methods of synthesizing magnesium ammonium phosphate are known. For example, U.S. Pat. No. 3,320,048 discloses a method in which either aqueous ammonia or liquid anhydrous ammonia is mixed with magnesium hydroxide and aqueous phosphoric acid to obtain magnesium ammonium phosphate granules, which are, in turn, dried and screened. U.S. Pat. No. 6,776,816 discloses a method in which animal manure is mixed with a magnesium-rich compound and an enzyme, such as a urease or uricase, to precipitate magnesium ammonium phosphate.

SUMMARY

Various exemplary embodiments of the present invention are directed to methods of producing a controlled release fertilizer including magnesium ammonium phosphate. In particular, methods of producing a controlled release fertilizer include intentional formation of magnesium ammonium phosphate within amino acid fermentation byproduct liquors. Amino acid fermentation byproduct liquors include a mixture of ammonium salts, simple nitrogen containing organic molecules such as amino acids, and nitrogen containing bacterial proteins. The latter two organic compounds are controlled or slow release in nature because, when applied to soil, the compounds must be metabolized by soil microorganisms and degraded into an inorganic form of nitrogen before the compounds can be utilized by plant roots. However, the amount of controlled or slow release nitrogen-containing compounds in amino acid fermentation byproduct liquors can be increased by converting some fraction of the constituent ammonium (i.e., from the ammonium salts mentioned above) into magnesium ammonium phosphate.

When constituent ammonium in amino acid fermentation byproduct liquors is converted into magnesium ammonium phosphate, the resulting magnesium ammonium phosphate will have a nitrogen release rate that is different and independent from the constituent organic sources (i.e., nitrogen containing organic molecules such as amino acids and nitrogen containing bacterial proteins in the amino acid fermentation byproduct liquors) because release of the nitrogen depends on solubility of the magnesium ammonium phosphate instead of microbial degradation. Magnesium ammonium phosphate has low solubility in water (<200 mg/kg), and this low solubility causes magnesium ammonium phosphate to slowly release nitrogen. Accordingly, converting a fraction of amino acid fermentation byproduct liquors into magnesium ammonium phosphate serves to diversify the types of controlled or slow release nitrogen sources in the amino acid fermentation byproduct liquors.

The present inventors surprisingly discovered, not only that magnesium ammonium phosphate can be formed by converting a fraction of amino acid fermentation byproduct liquors, but that magnesium ammonium phosphate can be formed more efficiently and over a wider pH range than is possible with pure systems (i.e., systems in which magnesium ammonium phosphate is obtained from pure sources of ammonium such as ammonium sulfate). In particular, employing amino acid fermentation byproduct liquors as an ammonium source when making magnesium ammonium phosphate permits production at pHs that can be at least as high as are employed in pure systems and at pHs that are lower than are employed in pure systems—even neutral or slightly acidic pHs. That is, employing amino acid fermentation byproduct liquors as an ammonium source when making magnesium ammonium phosphate allows for more consistent production of a controlled release fertilizer that is not as highly sensitive to pH as is the case in pure systems. The feasibility of employing amino acid fermentation byproduct liquors as an ammonium source when making magnesium ammonium phosphate can reduce or eliminate costs associated with pH adjustment. Accordingly, by employing methods of the present invention, it is possible to obtain a controlled or slow release fertilizer based on amino acid fermentation byproduct liquor that has an enhanced nitrogen profile. Moreover, methods of the present invention allow formation of magnesium ammonium phosphate in a way that is more efficient and less sensitive to pH than conventional methods.

In various exemplary embodiments, methods of preparing a controlled release fertilizer according to the present invention include obtaining an amino acid fermentation byproduct liquor, and converting ammonium in the amino acid fermentation byproduct liquor to magnesium ammonium phosphate to obtain the controlled release fertilizer.

In various exemplary embodiments, methods of preparing a controlled release fertilizer according to the present invention include obtaining an amino acid fermentation byproduct liquor, adding a source of phosphate to the amino acid fermentation byproduct liquor, adjusting pH of the amino acid fermentation byproduct liquor, and adding a source of magnesium to the amino acid fermentation byproduct liquor.

In various exemplary embodiments, methods of preparing a controlled release fertilizer according to the present invention include obtaining an amino acid fermentation byproduct liquor, adding a source of phosphate to the amino acid fermentation byproduct liquor to obtain an intermediate mixture, adjusting pH of the intermediate mixture, and adding a source of magnesium to the pH-adjusted intermediate mixture to obtain the controlled release fertilizer.

In various exemplary embodiments, processes for making soil adjuvants according to the present invention include producing a controlled release fertilizer as described herein, and processing the controlled release fertilizer into a form suitable for application to crops.

In various exemplary embodiments, soil adjuvants according to the present invention include soil adjuvants obtained by the methods described herein.

In various exemplary embodiments, processes of making agricultural products according to the present invention include preparing soil adjuvants by the methods described herein, applying the soil adjuvants to crops, and harvesting the crops to obtain the agricultural products.

In various exemplary embodiments, processes of making agricultural products according to the present invention include applying soil adjuvants as described herein to crops, and harvesting the crops to obtain the agricultural products.

In various exemplary embodiments, processes of making consumer products according to the present invention include preparing soil adjuvants by the methods described herein, applying the soil adjuvants to crops, harvesting the crops to obtain agricultural products, and processing the agricultural products to obtain the consumer products.

In various exemplary embodiments, processes of making consumer products according to the present invention include applying soil adjuvants as described herein to crops, harvesting the crops to obtain agricultural products, and processing the agricultural products to obtain the consumer products.

In various exemplary embodiments, processes of making industrial products according to the present invention include preparing soil adjuvants by the methods described herein, applying the soil adjuvants to crops, harvesting the crops to obtain agricultural products, and processing the agricultural products to obtain the industrial products.

In various exemplary embodiments, processes of making industrial products according to the present invention include applying soil adjuvants as described herein to crops, harvesting the crops to obtain agricultural products, and processing the agricultural products to obtain the industrial products.

DETAILED DESCRIPTION OF EXEMPLARY EMBODIMENTS

Various exemplary embodiments of the present invention are directed to methods of preparing controlled release fertilizers. In embodiments, methods include obtaining an amino acid fermentation byproduct liquor, and converting ammonium in the amino acid fermentation byproduct liquor to magnesium ammonium phosphate to obtain a controlled release fertilizer. While exemplary methods according to the present invention are focused on using amino acid fermentation byproducts as an ammonium source, it is also contemplated that alternative sources of ammonium, such as fungal or bacterial fermentation byproducts, could be used so long as such alternative sources can contribute ammonium ions in amounts sufficient to produce magnesium ammonium phosphate as described herein. In various exemplary embodiments, it is desirable that a potential ammonium source include from about 2 to about 10 weight percent ammonium.

In various exemplary embodiments, obtaining an amino acid fermentation byproduct liquor includes obtaining a byproduct liquor from fermentative production of at least one amino acid selected from the group consisting of arginine, histidine, isoleucine, leucine, lysine, methionine, phenylalanine, threonine, tryptophan, valine, glycine, serine, cysteine, tyrosine, alanine, aspartic acid, glutamic acid, proline, asparagine and glutamine. In some such embodiments, obtaining an amino acid fermentation byproduct liquor includes obtaining a byproduct liquor from fermentative production of at least one amino acid selected from the group consisting of glutamic acid, lysine, threonine and tryphophan. In some such embodiments, obtaining an amino acid fermentation byproduct liquor includes obtaining a byproduct liquor from fermentative production of at least one amino acid selected from the group consisting of lysine and threonine.

In embodiments, obtaining an amino acid fermentation byproduct liquor includes obtaining a byproduct liquor from fermentative production of at least one amino acid including bacterial cell mass. In various exemplary embodiments, amino acid fermentation byproduct liquors include condensed corn fermentation solubles (CCFS). CCFS includes byproduct media residue from fermentative production of amino acids, such as lysine and threonine. Particularly, CCFS may include spent fermentation media from production of amino acids, which remains after purification of the amino acids, including all residual bacterial cell mass, the media having been condensed to have a solids content between 20 and 60%. In alternative embodiments, obtaining an amino acid fermentation byproduct liquor includes obtaining a byproduct liquor from fermentative production of at least one amino acid from which bacterial cell mass has been removed. In various exemplary embodiments, amino acid fermentation byproduct liquors include residues from fermentative production of amino acids, such as lysine and threonine, from which bacterial cell mass has been removed such as, for example, fermentation mother liquor (ML). ML includes byproduct media from the fermentative production of amino acids, such as lysine and threonine, without bacterial cell mass. Particularly, ML may include the same components as CCFS, with the exception of bacterial cells mass—that is, ML includes spent media solubles from the production of amino acids, remaining after purification of the amino acids and after removal of bacterial cell mass. The method by which bacterial cell mass is removed is not particularly limited. In various exemplary embodiments, bacterial cell mass is removed from a byproduct liquor from fermentative production of at least one amino acid by microfiltration. However, the method by which bacterial cell mass is removed is not limited to microfiltration.

In embodiments, converting ammonium to magnesium ammonium phosphate includes adding a source of phosphate to the amino acid fermentation byproduct liquor, adjusting pH of the amino acid fermentation byproduct liquor, and adding a source of magnesium to the amino acid fermentation byproduct liquor. The order in which the components are added is not particularly limited, but it should be appreciated that a superior effect (e.g., in nitrogen recovery and conversion to insoluble forms of nitrogen) can be obtained by adding reactants in a particular order. For example, in some such embodiments, converting ammonium to magnesium ammonium phosphate includes adding a source of phosphate to the amino acid fermentation byproduct liquor to obtain an intermediate mixture, adjusting pH of the intermediate mixture, and adding a source of magnesium to the pH-adjusted intermediate mixture to obtain a composition including magnesium ammonium phosphate. In addition, the sources of phosphate and magnesium and the manner in which pH is adjusted are not particularly limited. However, again, it should be appreciated that embodiments of the present invention require particular sources of phosphate and magnesium and particular means for adjusting pH to achieve a superior effect, as discussed above.

In embodiments in which a source of phosphate is added to an amino acid fermentation byproduct liquor before other components (i.e., for pH adjustment and magnesium addition), it is desirable that the source of phosphate be mixed with the amino acid fermentation byproduct liquor for a time sufficient to allow dissolution and/or even distribution of the source of phosphate before the other components are added. In various exemplary embodiments, a source of magnesium is the final added component. The addition of the source of magnesium in such embodiments results in an exothermic reaction. Accordingly, it is desirable to complete the addition of the source of magnesium as quickly as possible, while ensuring that the source of magnesium is added in a manner that, e.g., prevents clumping of the source of magnesium in the mixture of other components. In various exemplary embodiments, the source of magnesium is added within 1 to 15 minutes, about 1 to about 15 minutes, 1 to 10 minutes, about 1 to about 10 minutes, 1 to 5 minutes, or about 1 to about 5 minutes. In various exemplary embodiments, the reaction mixture is constantly stirred while the source of magnesium is added. Good agitation during addition of the source of magnesium may improve formation of magnesium ammonium phosphate. After the source of magnesium is added, the reaction may be continued for a time sufficient to obtain an optimal amount of magnesium ammonium phosphate. In various exemplary embodiments, after the source of magnesium is added, the reaction may be carried out for 1 to 30 minutes, about 1 to about 30 minutes, 1 to 15 minutes, about 1 to about 15 minutes, 1 to 10 minutes, or about 1 to about 10 minutes. The starting temperature of reactants is not particularly limited.

In various exemplary embodiments, adding a source of phosphate includes adding a source of phosphate soluble in the amino acid fermentation byproduct liquor. In some such embodiments, adding a source of phosphate includes adding at least one source of phosphate selected from the group consisting of phosphoric acid, monoammonium phosphate, diammonium phosphate, sodium salts of phosphoric acid, potassium salts of phosphoric acid. The source of phosphate may be added in dry form or in solution. However, for some sources of phosphate a more desirable result is obtained by using one or the other form. In various exemplary embodiments, the source of phosphate is completely dissolved in the amino acid fermentation byproduct liquor before commencing addition of other components.

In embodiments, adjusting pH includes adjusting pH to a value in a range of from 6.0 to 8.6 or from about 6.0 to about 8.6. In further embodiments, adjusting pH includes adjusting pH to a value in a range of from 6.0 to 7.8 or from about 6.0 to about 7.8. In still further embodiments, adjusting pH includes adjusting pH to a value in a range of from 6.0 to 7.0 or from about 6.0 to about 7.0. The present inventors have discovered, as shown in the Examples below, that at lower pH, formation of insoluble nitrogen is more effective when using amino acid fermentation byproduct liquor in comparison with ammonium sulfate. In various exemplary embodiments, adjusting pH includes adjusting pH by adding at least one member selected from the group consisting of sources of sodium, sources of potassium and sources of ammonium. In some such embodiments, adjusting pH includes adjusting pH by adding at least one member selected from the group consisting sodium hydroxide, calcium oxide, potassium hydroxide and ammonium hydroxide. Although this effect is reduced when using amino acid fermentation byproduct liquors in comparison with, e.g., ammonium sulfate, it should be appreciated that addition of a source of magnesium after pH is adjusted may result in a further increase in pH. Accordingly, in various exemplary embodiments, the pH after addition of the source of magnesium is from 6.2 to 9.0, or from about 6.2 to about 9.0. In further embodiments, the pH after addition of the source of magnesium is from 6.2 to 8.0, or from about 6.2 to about 8.0. In general, magnesium ammonium phosphate formation occurs under more alkaline conditions. However, the pKa of ammonium is 9.2 and increasing the alkalinity of the amino acid fermentation byproduct liquor causes a portion of the ammonium to dissociate into the $NH_3$ form and elute as a gas, resulting in loss of nitrogen.

In embodiments, adding a source of magnesium includes adding at least one member selected from the group consisting of magnesium oxide and magnesium hydroxide. The source of magnesium may be added in dry form or in solution.

In various exemplary embodiments of the methods according to the present invention, the amino acid fermentation byproduct liquor, the source of phosphate and the source of magnesium are present in amounts sufficient to provide ammonium and phosphate in a molar ratio of from 20:1 to 1:20, from about 20:1 to about 1:20, from 15:1 to 1:15, from about 15:1 to about 1:15, from 10:1 to 1:10, or from about 10:1 to about 1:10, and magnesium and phosphate in a molar ratio of from 10:1 to 1:10, from about 10:1 to about 1:10, from 5:1 to 1:5, from about 5:1 to about 1:5, from 2:1 to 1:2, or from about 2:1 to about 1:2. In embodiments, the amino acid fermentation byproduct liquor, the source of phosphate and the source of magnesium are present in amounts sufficient to provide ammonium and phosphate in a molar ratio of preferably from 15:1 to 1:15 and more preferably from 10:1 to 1:10, and magnesium and phosphate in a molar ratio of preferably from 5:1 to 1:5 and more preferably from 2:1 to 1:2.

In embodiments, methods according to the present invention further include drying the controlled release fertilizer. In still further embodiments, methods according to the present invention include granulating the dried controlled release fertilizer. In various exemplary embodiments, the controlled release fertilizer is dried so that the product has a moisture content of from 1 to 20%, from about 1 to about 20%, from 3 to 17%, from about 3 to about 17%, from 5 to 14%, or from about 5 to about 14%. Drying may be carried out in any suitable apparatus including, but not limited to, a drum dryer, a fluid bed dryer, a belt dryer, a disc dryer, a flush dryer, a rotary dryer, a rotary vacuum dryer, a steam tube dryer, a tray dryer, a turbo dryer, a vacuum dryer or a conical dryer. In various exemplary embodiments, clay or beet pulp may be used as carrier for drying. The dried controlled release fertilizer may be granulated by any suitable means, including, but not limited to, pan pelletizers, pin mixers, pellet machines and fluidized bed dryers. Granule size affects the release rate of magnesium ammonium phosphate such that, for example, larger granules will have a slower release rate due to the increased time required for the larger granules to dissolve in soil moisture. In various exemplary embodiments, the dried controlled release fertilizer may be granulated to have a granule size of from 0.1 mm to 10 mm, from about 0.1 mm to about 10 mm, from 0.5 mm to 5 mm, from about 0.5 mm to about 5 mm, from 1 mm to 3 mm, or from about 1 mm to about 3 mm.

The present invention is directed to processes for making soil adjuvants. In various exemplary embodiments, processes for making a soil adjuvant may include producing a controlled release fertilizer by the methods described above, and processing the controlled release fertilizer into a form suitable for application to crops. The present invention is further directed to soil adjuvants obtained by such processes.

The present invention is further directed to processes of making agricultural products. In various exemplary embodiments, such processes include preparing soil adjuvants by the methods described above, applying the soil adjuvants to crops (e.g., in wet or dry form), and harvesting the crops to obtain agricultural products. Exemplary crops may include food crops and ornamental crops. Exemplary food crops may include fruits, vegetables and grains. Exemplary ornamental crops may include turfgrass, trees, shrubs and flowers. In further exemplary embodiments, such processes may include applying an already prepared soil adjuvant to crops, and harvesting the crops to obtain agricultural products.

The present invention is further directed to processes of making consumer products. In various exemplary embodiments, such processes include preparing soil adjuvants by the methods described above, applying the soil adjuvants to crops as described above, harvesting the crops to obtain agricultural products, and processing the agricultural products to obtain consumer products. In further exemplary embodiments, such processes may include applying an already prepared soil adjuvant to crops, harvesting the crops to obtain agricultural products, and processing the agricultural products to obtain consumer products.

The present invention is further directed to processes of making industrial products. In various exemplary embodiments, such processes include preparing soil adjuvants by the methods described above, applying the soil adjuvants to crops as described above, harvesting the crops to obtain agricultural products, and processing the agricultural products to obtain industrial products. In further exemplary embodiments, such processes may include applying an already prepared soil adjuvant to crops, harvesting the crops to obtain agricultural products, and processing the agricultural products to obtain industrial products.

Other features of the invention will become apparent from the following Examples, which are provided for the purposes of illustration of the invention and are not intended to be limiting.

EXAMPLES

Example 1

Components of magnesium ammonium phosphate ($NH_4$, $PO_4$, and $Mg$) were combined in various orders to identify a superior addition sequence for preparation of magnesium ammonium phosphate, while minimizing $NH_4$ loss. Ammonium, magnesium and phosphate were obtained from ammonium hydroxide, magnesium oxide, and 85% phosphoric acid, respectively. Amounts of added magnesium oxide and phosphoric acid were calculated based on amounts of ammonium hydroxide used to provide ammonium, magnesium and phosphate in a molar ratio of 1:1:1. Samples were mixed at 250 rpm for 5 minutes following addition of the last ingredient. The products were then dried in a forced air oven at 50° C. until there was little or no change in mass. The products were weighed after being removed from the oven and ground in a blender.

Total ammoniacal nitrogen was measured by alkali distillation and collection in 4% boric acid with phenolphthalein indicator followed by titration with sulfuric acid. Samples of the dried products were weighed prior to and after being placed in a 110° C. oven for 24 hrs to determine dry matter %. 1.5 g samples of the dried products were dissolved in 100 g of water. After 24 hrs the solutions were filtered through Whatman 54 filter paper and the filtrate was distilled to determine soluble ammoniacal nitrogen content. Insoluble ammoniacal nitrogen content was quantified by subtracting soluble ammoniacal nitrogen content from the determined total ammoniacal nitrogen. To determine the relative efficiency of each sequence of additions, insoluble ammoniacal nitrogen content (moles) was divided by the amount of added phosphate (moles). The amount of retained ammoniacal nitrogen in the dried products was determined by dividing total ammoniacal nitrogen content in each of the dried products by the total ammoniacal nitrogen content of the employed nitrogen sources. The results are shown in TABLE 1 below.

TABLE 1

| Sequence of Additions | | | % of $NH_4$ Retained | Moles of Insoluble Ammoniacal Nitrogen Per Mole of Phosphate Added |
|---|---|---|---|---|
| Step 1 | Step 2 | Step 3 | | |
| $PO_4$ | $Mg$ | $NH_4$ | 87 | 0.60 |
| $Mg$ | $NH_4$ | $PO_4$ | 87 | 0.33 |
| $NH_4$ | $PO_4$ | $Mg$ | 100 | 1.00 |

Adding a phosphate source and then a magnesium source to an ammonium source was determined to be the most effective sequence for obtaining magnesium ammonium phosphate.

Due to the effectiveness of first adding phosphate to the ammoniacal nitrogen source and then lastly adding magnesium, such mixing order was employed in the following reactions.

Example 2

Different sources of ammonium were used to prepare magnesium ammonium phosphate in different amounts to identify superior reactants and amounts for preparation of magnesium ammonium phosphate, while minimizing $NH_4$ loss. Ammonium sulfate (AS), condensed corn fermentation solubles (CCFS) and fermentation mother liquor (ML) were evaluated as potential ammonium sources. Phosphate and magnesium were added in sequence in the amounts set forth in TABLE 2 below using 85% phosphoric acid as a phosphate source and magnesium oxide as a magnesium source. Samples were mixed at 250 rpm as the components were added and pH was monitored. Following addition of phosphoric acid, pH of the samples was adjusted to 6 with 50% potassium hydroxide. The mixing rate was increased to 300 rpm for 5 minutes after MgO was added. The resulting products were processed and analyzed as described above with respect to Example 1. The results are shown in TABLE 2 below.

TABLE 2

| Source of Ammoniacal Nitrogen | NH$_4$:PO$_4$:Mg Molar Ratio | % of NH$_4$ Retained | Moles of Insoluble Ammoniacal Nitrogen Per Mole of Phosphate Added |
|---|---|---|---|
| AS | 3:1:1 | 94 | 0.44 |
| CCFS | 3:1:1 | 95 | 0.66 |
| ML | 3:1:1 | 93 | 0.63 |
| AS | 2:1:1 | 83 | 0.61 |
| CCFS | 2:1:1 | 85 | 0.56 |
| ML | 2:1:1 | 88 | 0.45 |
| AS | 1:1:1 | 62 | 0.52 |
| CCFS | 1:1:1 | 81 | 0.53 |
| ML | 1:1:1 | 69 | 0.46 |
| AS | 3:1:2 | 82 | 0.95 |
| CCFS | 3:1:2 | 83 | 1.00 |
| ML | 3:1:2 | 72 | 0.99 |
| AS | 2:1:2 | 71 | 0.95 |
| CCFS | 2:1:2 | 76 | 0.93 |
| ML | 2:1:2 | 80 | 0.86 |

Ammoniacal nitrogen recovery varies between ammonia sources. Ammoniacal nitrogen recovery when using CCFS as an ammonium source was more than 10% higher when reactants were employed in a 1:1:1 ratio, as compared with other ratios. When employing a 3:1:2 ratio of reactants, ammoniacal nitrogen recovery was more than 10% lower when using ML as an ammonium source than when using other ammonium sources. Mean ammoniacal nitrogen recovery and mean moles of insoluble ammoniacal nitrogen per mole of phosphate added are set forth in TABLE 3 below.

TABLE 3

| Ammonium Source | Mean % of NH$_4$ Retained | Mean Moles of Insoluble Ammoniacal Nitrogen Per Mole of Phosphate Added |
|---|---|---|
| AS | 78 | 0.69 |
| CCFS | 84 | 0.74 |
| ML | 80 | 0.68 |

Mean ammoniacal nitrogen recovery for each ammonium source indicated ammonium sulfate to be the lowest and CCFS to be the highest. CCFS was also more effective in insoluble ammoniacal nitrogen conversion than both ammonium sulfate and ML. Products obtained using ML as an ammonium source took somewhat longer to dry and, during the reaction, had the potential to boil over in the reaction vessel.

Although the use of ML as a source of ammoniacal nitrogen raises some issues due to the length of time required for drying, the potential for boiling over, and the lower insoluble ammoniacal nitrogen conversion and the ammoniacal nitrogen recovery relative to CCFS, as indicated above, ML remains an effective source of ammoniacal nitrogen. The higher insoluble ammoniacal nitrogen conversion and higher ammoniacal nitrogen recovery, when using CCFS, as opposed to ammonium sulfate, as an ammonium source, indicated that CCFS was a superior source of ammonium relative to ammonium sulfate.

Example 3

Different pHs were used to prepare magnesium ammonium phosphate using CCFS and ammonium sulfate as ammonium sources to identify superior reaction conditions for preparation of magnesium ammonium phosphate, while minimizing NH$_4$ loss. Samples were prepared as set forth in TABLE 4 below according to the procedures described above with respect to Example 2. The procedure of Example 2 was varied by adjusting pH to different levels prior to addition of magnesium oxide. The resulting products were processed and analyzed as described above with respect to Example 1. The results are set forth in TABLE 4 below.

TABLE 4

| Ammonium Source | NH$_4$:PO$_4$:Mg Molar Ratio | pH After Addition of KOH | pH After Addition of MgO | % of NH$_4$ Retained | Moles of Insoluble Ammoniacal Nitrogen Per Mole of Phosphate Added |
|---|---|---|---|---|---|
| AS | 3:1:1 | 6.19 | 6.50 | 92.2 | 0.28 |
| CCFS | 3:1:1 | 6.20 | 6.38 | 88.3 | 0.51 |
| AS | 3:1:1 | 7.02 | 7.30 | 86.8 | 0.38 |
| CCFS | 3:1:1 | 7.02 | 7.23 | 83.5 | 0.48 |
| AS | 3:1:1 | 8.55 | 8.87 | 66.2 | 0.30 |
| CCFS | 3:1:1 | 8.55 | 8.74 | 69.5 | 0.37 |
| AS | 10:1:1 | 6.00 | 6.58 | 97.3 | 0.57 |
| CCFS | 10:1:1 | 6.00 | 6.24 | 92.8 | 0.70 |
| AS | 10:1:1 | 6.99 | 7.46 | 94.8 | 0.77 |
| CCFS | 10:1:1 | 7.00 | 7.38 | 88.4 | 0.74 |

At a 3:1:1 ratio of reactants, regardless of pH, CCFS as an ammonium source yielded higher insoluble ammoniacal nitrogen conversion than ammonium sulfate as an ammonium source. At a 3:1:1 ratio of reactants, CCFS as an ammonium source yielded highest insoluble ammoniacal nitrogen conversion when pH is adjusted to approximately 6.2, while ammonium sulfate as an ammonium source yielded highest insoluble ammoniacal nitrogen conversion when pH is adjusted to approximately 7.0. Recovery of ammoniacal nitrogen is highest when pH is adjusted to approximately 6.2 and recovery of ammoniacal nitrogen decreases as pH increases. At a 3:1:1 ratio of reactants, when pH was adjusted to approximately 6.2 and approximately 7.0 ammonium sulfate as an ammonium source yielded a higher recovery than CCFS, and at a pH of approximately 8.5 CCFS as an ammonium source yielded a higher recover than ammonium sulfate.

At a 10:1:1 ratio of reactants and a pH of approximately 6.0, CCFS as an ammonium source yielded higher insoluble ammoniacal nitrogen conversion than ammonium sulfate as an ammonium source. At a 10:1:1 ratio of reactants, both ammonium sulfate and CCFS yielded greatest amounts of insoluble ammoniacal nitrogen conversion at a pH of approximately 7.0, with ammonium sulfate being slightly higher than CCFS. At a 10:1:1 ratio of reactants, when pH was adjusted to approximately 7.0, ammonium sulfate as an ammonium source yielded a higher ammoniacal nitrogen recovery than CCFS.

The pH of the reaction mixture during preparation of magnesium ammonium phosphate had a significant effect on production of insoluble ammoniacal nitrogen conversion, as between CCFS and ammonium sulfate as ammoniacal nitrogen sources. The higher rate of insoluble ammoniacal nitrogen production, when using CCFS as an ammonium source over varying pH made CCFS more favorable as an ammonium source than ammonium sulfate, because less pH adjustment was required to obtain the same amount of insoluble ammoniacal nitrogen conversion. Moreover, in some applications, an acidic fertilizer is desirable. Employing CCFS as an ammonium source permits the retention of an acidic character without compromising insoluble ammoniacal nitrogen conversion.

Example 4

Different sources of phosphate were used to prepare magnesium ammonium phosphate to identify superior reaction conditions for preparation of magnesium ammonium phosphate, while minimizing $NH_4$ loss. Samples were prepared as set forth in TABLE 5 below according to the procedures described above with respect to Example 2. The procedure of Example 2 was varied by using either 85% phosphoric acid, dry soluble monoammonium phosphate (MAP) or a 50% solution of MAP in water. The resulting products were processed and analyzed as described above with respect to Example 1. The results are set forth in TABLE 5 below.

TABLE 5

| Phosphate Source | $NH_4:PO_4:Mg$ Molar Ratio | % of $NH_4$ Retained | Moles of Insoluble Ammoniacal Nitrogen Per Mole of Phosphate Added |
|---|---|---|---|
| 85% $H_3PO_4$ | 3:1:1 | 94.5 | 0.66 |
| Dry MAP | 3:1:1 | 97.7 | 0.61 |
| 50% MAP Solution | 3:1:1 | 94.8 | 0.39 |
| 85% $H_3PO_4$ | 2:1:1 | 85.3 | 0.56 |
| Dry MAP | 2:1:1 | 97.4 | 0.48 |
| 50% MAP Solution | 2:1:1 | 95.8 | 0.32 |
| 85% $H_3PO_4$ | 3:1:2 | 83.3 | 1.00 |
| Dry MAP | 3:1:2 | 94.6 | 0.98 |
| 50% MAP Solution | 3:1:2 | 85.7 | 0.88 |
| 85% $H_3PO_4$ | 2:1:2 | 76.1 | 0.93 |
| Dry MAP | 2:1:2 | 93.0 | 0.95 |
| 50% MAP Solution | 2:1:2 | 87.1 | 0.96 |
| 85% $H_3PO_4$ | 10:1:1 | 98.4 | 0.77 |
| Dry MAP | 10:1:1 | 98.5 | 0.73 |
| 50% MAP Solution | 10:1:1 | 92.7 | 0.67 |
| 85% $H_3PO_4$ | 15:1:1 | 98.0 | 0.62 |
| Dry MAP | 15:1:1 | 98.0 | 0.65 |
| 50% MAP Solution | 15:1:1 | 96.1 | 0.59 |
| 85% $H_3PO_4$ | 20:1:1 | 98.8 | 0.86 |
| Dry MAP | 20:1:1 | 97.5 | 0.52 |
| 50% MAP Solution | 20:1:1 | 97.3 | 0.50 |

Mean ammoniacal nitrogen recovery and mean moles of insoluble ammoniacal nitrogen per mole of phosphate added are set forth in TABLE 6 below.

TABLE 6

| Phosphate Source | Mean % of $NH_4$ Retained | Mean Moles of Insoluble Ammoniacal Nitrogen Per Mole of Phosphate Added |
|---|---|---|
| 85% $H_3PO_4$ | 90.6 | 0.77 |
| Dry MAP | 96.7 | 0.70 |
| 50% MAP Solution | 92.8 | 0.62 |

Employing dry MAP as a phosphate source in preparing magnesium ammonium phosphate resulted in higher ammoniacal nitrogen recovery than phosphoric acid. Using MAP in solution as a phosphate source provided slightly higher ammoniacal nitrogen recover than using phosphoric acid. Conversion of ammoniacal nitrogen to insoluble ammoniacal nitrogen was highest in formulations using phosphoric acid as a phosphate source and was lowest in formulations using MAP solution in solution as a phosphate source.

Both phosphoric acid and soluble MAP could be used as a source of phosphate in preparing magnesium ammonium phosphate, as both provide beneficial results. MAP provides for higher ammoniacal nitrogen recovery, while phosphoric acid provides for higher insoluble ammoniacal nitrogen conversion. Due to its ammoniacal nitrogen content, MAP provides the additional benefit of increasing nitrogen content in the final product.

Example 5

Different sources of magnesium were used to prepare magnesium ammonium phosphate to identify superior reaction conditions for preparation of magnesium ammonium phosphate, while minimizing $NH_4$ loss. Samples were prepared as set forth in TABLE 7 below according to the procedures described above with respect to Example 2. The procedure of Example 2 was varied by using either dry magnesium oxide, a 50% solution of magnesium nitrate in water or dry magnesium nitrate. The resulting products were processed and analyzed as described above with respect to Example 1. The results are set forth in TABLE 7 below.

TABLE 7

| Magnesium Source | $NH_4:PO_4:Mg$ Molar Ratio | % of $NH_4$ Retained | Moles of Insoluble Ammoniacal Nitrogen Per Mole of Phosphate Added |
|---|---|---|---|
| MgO | 3:1:1 | 97.0 | 0.65 |
| Dry $MgNO_3$ | 3:1:1 | 87.5 | 0.00 |
| 50% $MgNO_3$ Solution | 3:1:1 | 100.3 | 0.01 |
| MgO | 2:1:1 | 94.2 | 0.59 |
| Dry $MgNO_3$ | 2:1:1 | 105.0 | 0.00 |
| 50% $MgNO_3$ Solution | 2:1:1 | 103.9 | 0.06 |
| MgO | 1:1:1 | 77.1 | 0.54 |
| Dry $MgNO_3$ | 1:1:1 | 102.4 | 0.00 |

Employing magnesium nitrate as a magnesium source was not effective in converting ammoniacal nitrogen to insoluble ammoniacal nitrogen. Recovery of ammoniacal nitrogen was higher when using magnesium nitrate formulations as magnesium sources than when using magnesium oxide.

The higher than 100% ammoniacal nitrogen recovery when using magnesium nitrate as a magnesium source was likely due to ammoniacal nitrogen contamination in the magnesium nitrate, or conversion of some of the nitrate to ammoniacal nitrogen during the formulation procedure. Although magnesium nitrate adds ammoniacal nitrogen to the final product in the reaction, which would be beneficial in the fertilizer, it was not effective at insoluble ammoniacal nitrogen conversion and thus is not a superior magnesium source in preparation of magnesium ammonium phosphate.

Example 6

Byproduct media residue from fermentative production of lysine and threonine were obtained. The byproduct media residue included residue with residual cell mass and residue without residual cell mass. The residues included about 25% ammonium sulfate along with free amino acids, peptides, sugars, organic acids, minerals and other components resulting from the fermentation process. The residues were compared with pure ammonium sulfate to identify superior sources of ammoniacal nitrogen for production of magnesium ammonium phosphate. Magnesium ammonium phosphate was prepared by combining the reactants shown in TABLE 8 below. The reactants were combined in the order shown in TABLE 8. The pH of the respective combined ammonium source and phosphate source was increased by adding sodium hydroxide, calcium oxide, potassium hydroxide or ammonium hydroxide before adding the magnesium source. After mixing, the pH of the respective samples was recorded and the samples were dried in a forced air oven at 60° C.

TABLE 8

| | Reactant Amount | | | | | | | | | |
|---|---|---|---|---|---|---|---|---|---|---|
| | Source of ammonium | | | | Source for pH adjustment | | | | | Source |
| Sample | Residue with Cell Mass (g) | Residue without Cell Mass (g) | 25% (NH$_4$)$_2$SO$_4$ (g) | Source of phosphate 85% H$_3$PO$_4$ (g) | NaOH (g) | NaCl (g) | CaO (g) | KOH (g) | NH$_3$ aq. (ml) | of Mg MgO (g) |
| 6-1 | 200 | | | 90 | | | | | | 32 |
| 6-2 | 200 | | | 45 | | | | | | 16 |
| 6-3 | 200 | | | 22 | | | | | | 8 |
| 6-4 | 200 | | | 90 | | | | | 80 | 32 |
| 6-5 | 200 | | | 45 | | | | | 40 | 16 |
| 6-6 | 200 | | | 22 | | | | | 20 | 8 |
| 6-7 | 200 | | | 22 | | | | | | 8 |
| 6-8 | | | 200 | 45 | 20 | | | | | 16 |
| 6-9 | | | 200 | 45 | 20 | | | | | 16 |
| 6-10 | | | 200 | 22 | 10 | | | | | 8 |
| 6-11 | | | 200 | 22 | 10 | | | | | 8 |
| 6-12 | | 200 | | 45 | 20 | | | | | 16 |
| 6-13 | | 200 | | 90 | | | | | 94 | 32 |
| 6-14 | | 200 | | 90 | 40 | | | | | 32 |
| 6-15 | | 200 | | 45 | | | | | | 16 |
| 6-16 | | 200 | | 45 | | 10 | | | | 16 |
| 6-17 | | 200 | | 90 | | | | 80 | | 32 |
| 6-18 | | 200 | | 90 | | | 20 | | | 32 |
| 6-19 | | 200 | | 90 | | | 40 | | | |
| 6-20 | | | 200 | 45 | | | | 36 | | 16 |
| 6-21 | | | 200 | 23 | | | | 19 | | 8 |
| 6-22 | | 200 | | 37 | | | | 32 | | 13 |
| 6-23 | | 200 | | 37 | | | | 55 | | |
| 6-24 | | 200 | | 37 | | | | | | 48 |
| 6-25 | | 200 | | 46 | | | 35 | | | 16 |
| 6-26 | | | 200 | 22 | 10 | | | | | 8 |
| 6-27 | 200 | | | 90 | 40 | | | | | 32 |
| 6-28 | 200 | | | 45 | | | | | | 16 |

A total amount of ammoniacal nitrogen in the dried samples was determined by alkali distillation and collection in 4% boric acid with phenolphthalein indicator followed by titration with sulfuric acid. Water insoluble ammonia nitrogen content was determined by subtracting the amount of soluble ammoniacal nitrogen in 1.5 g of a dried sample stirred in 100 g deionized water for 1 hr from the total amount ammoniacal nitrogen. The results are shown in TABLE 9 below.

TABLE 9

| Sample | NH$_4$:PO$_4$:Mg Molar Ratio | pH after addition of MgO | total solids % at mixing | total AN in dried sample, % | g insol. AN per 100 g total AN | Moles Insol. AN Per Mole of PO$_4$ Added |
|---|---|---|---|---|---|---|
| 6-1 | 1.25:1:1 | 4.1 | 57 | 4.06 | 2 | 0.01 |
| 6-2 | 2.5:1:1 | 4.9 | 54 | 5.26 | 3 | 0.04 |
| 6-3 | 5:1:1 | 5 | 48 | 6.68 | 3 | 0.08 |
| 6-4 | 2.5:1:1 | 7.9 | 52 | 10.52 | 31 | 0.60 |
| 6-5 | 3:1:1 | 8 | 50 | 10.13 | 23 | 0.59 |
| 6-6 | 6.25:1:1 | 7.9 | 49 | 10.09 | 15 | 0.64 |
| 6-7 | 5:1:1 | 5 | 52 | 7.25 | 0 | 0.00 |
| 6-8 | 1.5:1:1 | 7.7 | 44 | 5.57 | 29 | 0.24 |
| 6-9 | 1.5:1:1 | 7.6 | 43 | 4.56 | 32 | 0.26 |
| 6-10 | 3:1:1 | 7.5 | 40 | 9.31 | 25 | 0.42 |
| 6-11 | 3:1:1 | 7 | 44 | 7.41 | 10 | 0.18 |
| 6-12 | 2.5:1:1 | 7.5 | 69 | 7.45 | 19 | 0.42 |
| 6-13 | 2.75:1:1 | 7.5 | 64 | 10.36 | 23 | 0.50 |
| 6-14 | 1.25:1:1 | 7.5 | 77 | 5.04 | 45 | 0.47 |
| 6-15 | 2.5:1:1 | 5 | 67 | 8.89 | 2 | 0.05 |
| 6-16 | 2.5:1:1 | 5 | 68 | 8.87 | 2 | 0.05 |
| 6-17 | 1.25:1:1 | 7.5 | 79 | 5.29 | 47 | 0.58 |
| 6-18 | 1.25:1:1 | — | 74 | 7.03 | 20 | 0.27 |
| 6-19 | 1.25:1:0 | — | 60 | 7.19 | 2 | 0.02 |
| 6-20 | 1.5:1:1 | 6.8 | 47 | 6.13 | 41 | 0.52 |

TABLE 9-continued

| Sample | NH$_4$:PO$_4$:Mg Molar Ratio | pH after addition of MgO | total solids % at mixing | total AN in dried sample, % | g insol. AN per 100 g total AN | Moles Insol. AN Per Mole of PO$_4$ Added |
|---|---|---|---|---|---|---|
| 6-21 | 3:1:1 | 6.2 | 66 | 9.01 | 13 | 0.33 |
| 6-22 | 2.6:1:1 | — | 66 | 7.03 | 24 | 0.57 |
| 6-23 | 2.6:1:0 | 8.2 | 65 | — | — | 0.00 |
| 6-24 | 2.7:1:3.2 | — | 70 | 5.3 | 53 | 1.01 |
| 6-25 | 2.5:1:1 | — | 71 | 1.5 | 29 | 0.13 |
| 6-26 | 3:1:1 | 7.5 | 25 | 11.09 | 20 | 0.41 |
| 6-27 | 1.25:1:1 | — | 61 | 3.11 | 95 | 0.49 |
| 6-28 | 2.5:1:1 | — | 53 | 3.38 | 60 | 0.45 |

Insoluble ammoniacal nitrogen formation was quantified as moles of insoluble ammoniacal nitrogen divided per mole of added phosphate. Magnesium ammonium phosphate was not formed under conditions with a final pH of less than 5. Using byproduct media residue with and without residual cell mass appears to result in efficient production of magnesium ammonium phosphate. That is, the presence of cell mass does not appear to have substantial effect on magnesium ammonium phosphate production. Employing an excess of magnesium appears to increase efficiency of magnesium ammonium phosphate production. Preparing magnesium ammonium phosphate using pure ammonium sulfate as an ammonium source appears to result in lower efficiency of magnesium ammonium phosphate production in comparison with byproduct media residue under like pH conditions. Substituting potassium for magnesium, to prepare potassium ammonium phosphate, was not effective in yielding insoluble ammoniacal nitrogen and thus would not effective in producing controlled release fertilizer. Adjusting pH with calcium after magnesium oxide was added does not result in effective production of insoluble ammoniacal nitrogen when phosphoric acid was used as a phosphate source. It is believed that calcium bonds with soluble phosphate, preventing the phosphate from being available for production of magnesium ammonium phosphate.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of preparing a controlled release fertilizer, comprising:
    obtaining condensed corn fermentation solubles; and
    treating said condensed corn fermentation solubles with a source of magnesium and a source of phosphate to obtain a controlled release fertilizer comprising magnesium ammonium phosphate and residual bacterial cell mass,
    wherein the condensed corn fermentation solubles comprise a byproduct liquor from fermentative production of at least one amino acid selected from the group consisting of arginine, histidine, isoleucine, leucine, lysine, methionine, phenylalanine, threonine, tryptophan, valine, glycine, serine, cysteine, tyrosine, alanine, aspartic acid, glutamic acid, proline, asparagine and glutamine.

2. The method of claim 1, wherein the condensed corn fermentation solubles comprise a byproduct liquor from fermentative production of at least one amino acid selected from the group consisting of glutamic acid, lysine, threonine and tryptophan.

3. The method of claim 1, wherein the condensed corn fermentation solubles comprise a byproduct liquor from fermentative production of at least one amino acid selected from the group consisting of lysine and threonine.

4. The method of claim 1, wherein treating the condensed corn fermentation solubles comprises:
    adding the source of phosphate to the condensed corn fermentation solubles;
    adjusting pH of the condensed corn fermentation solubles; and
    adding the source of magnesium to the condensed corn fermentation solubles.

5. The method of claim 1, wherein treating the condensed corn fermentation solubles comprises:
    adding the source of phosphate to the condensed corn fermentation solubles to obtain an intermediate mixture;
    adjusting pH of the intermediate mixture; and
    adding the source of magnesium to the pH-adjusted intermediate mixture to obtain the controlled release fertilizer.

6. The method of claim 5, wherein adding the source of phosphate comprises adding a source of phosphate soluble in the condensed corn fermentation solubles.

7. The method of claim 5, wherein adding the source of phosphate comprises adding at least one source of phosphate selected from the group consisting of phosphoric acid, monoammonium phosphate, diammonium phosphate, sodium salts of phosphoric acid, and potassium salts of phosphoric acid.

8. The method of claim 5, wherein adjusting pH comprises adjusting pH to a value in a range of from 6.0 to 8.6.

9. The method of claim 5, wherein adjusting pH comprises adjusting pH to a value in a range of from 6.0 to 7.0.

10. The method of claim 5, wherein adjusting pH comprises adjusting pH by adding at least one member selected from the group consisting of sources of sodium, sources of potassium and sources of ammonium.

11. The method of claim 5, wherein adjusting pH comprises adjusting pH by adding at least one member selected from the group consisting of sodium hydroxide, calcium oxide, potassium hydroxide and ammonium hydroxide.

12. The method of claim 5, wherein adding the source of magnesium comprises adding at least one member selected from the group consisting of magnesium oxide and magnesium hydroxide.

13. The method of claim 5, wherein the pH after addition of the source of magnesium is in a range of from 6.2 to 9.0.

14. The method of claim 5, wherein the pH after addition of the source of magnesium is in a range of from 6.2 to 8.0.

15. The method of claim 5, wherein ammonium in the condensed corn fermentation solubles, the source of phosphate and the source of magnesium are present in amounts sufficient to provide:
 ammonium and phosphate in a molar ratio of from 20:1 to 1:20; and
 magnesium and phosphate in a molar ratio of from 10:1 to 1:10.

16. The method of claim 1, further comprising drying the controlled release fertilizer.

17. The method of claim 16, further comprising granulating the dried controlled release fertilizer.

* * * * *